United States Patent [19]
Kaneko et al.

[11] Patent Number: 5,376,251
[45] Date of Patent: Dec. 27, 1994

[54] CARBON MICRO-SENSOR ELECTRODE AND METHOD FOR PREPARING IT

[75] Inventors: Hiroko Kaneko, Tsukuba; Masahiro Yamada, Inashiki; Akira Negishi, Matsudo; Takamasa Kawakubo; Yoshihisa Suda, both of Fujioka, all of Japan

[73] Assignees: Agency of Industrial Science and Technology; Mitsubishi Pencil Kabushiki Kaisha, both of Tokyo, Japan

[21] Appl. No.: 147,780

[22] Filed: Nov. 4, 1993

Related U.S. Application Data

[62] Division of Ser. No. 905,767, Jun. 29, 1992, Pat. No. 5,281,319.

[30] Foreign Application Priority Data

Jul. 9, 1991 [JP] Japan ................... 3-193719

[51] Int. Cl.$^5$ ........................... G01N 27/26
[52] U.S. Cl. ................... 204/294; 204/403; 204/415; 435/817
[58] Field of Search ............ 204/294, 291, 403, 416, 204/415; 435/817

[56] References Cited

U.S. PATENT DOCUMENTS

| 4,311,682 | 1/1982 | Miyazaki et al. | 423/448 |
|---|---|---|---|
| 4,544,641 | 10/1985 | Dumas et al. | 501/87 |
| 4,908,115 | 3/1990 | Morita et al. | 204/294 |
| 4,985,184 | 1/1991 | Takahashi et al. | 264/6 |
| 5,002,651 | 3/1991 | Shaw et al. | 204/294 |
| 5,273,639 | 12/1993 | Kaneko et al. | 204/294 |

FOREIGN PATENT DOCUMENTS

| 58-12201 | 3/1983 | Japan . |
|---|---|---|
| 4-74957 | 3/1992 | Japan . |
| 4-74958 | 3/1992 | Japan . |

OTHER PUBLICATIONS

Extended Abstracts vol. II for 40th ISE (International Society of Electrochemistry) meeting held in Kyota, Japan Sep. 17-22, 1989 Kaneko et al., "Electrochemical Behavior of GRC Electrodes for Voltammetry".

Extended Abstracts vol. II for 40th ISE (International Society of Electrochemistry) meeting held in Kyota, Japan Sep. 17-22, 1989 Abe, et al., "Fabrication and Application of Micro-electrode to In-vivo Voltammetry".

Extended Abstracts vol. II for 40th ISE (International Society of Electrochemistry) meeting held in Kyota, Japan Sep. 17-22, 1989, Kaneko et al., "Redox Reactions of Vanadium Ions on GRC and Carbon Fiber Electrodes".

The Japan Association for the Advancement of Science, The 117th Committee Carbon Materials 117-21-3-C-1 held Feb. 1, 1991, Kawakubo et al. "Preparation of Micro-Electrode Using Graphite/Carbon Compos- (List continued on next page.)

*Primary Examiner*—John Niebling
*Assistant Examiner*—Bruce F. Bell
*Attorney, Agent, or Firm*—Darby & Darby

[57] ABSTRACT

A carbon micro-sensor electrode is disclosed which is prepared by impregnating, adsorbing or chemically modifying a pure composite carbon wire having many micropores extending to its surface and interior with a reactant such as an enzyme, a metal complex compound, an organic compound or a metabolite; and a method for preparing this carbon micro-sensor electrode is also disclosed.

The above-mentioned electrode can be used for a long period of time, since the reactant is received in the many micropores. Furthermore, after used, the electrode may be cut off to expose a new electrode surface, and this new electrode surface may be coated with a material which does not impede an electrode reaction, whereby the reactant can be prevented from flowing out. Thus, the carbon micro-sensor electrode of the present invention can be repeatedly utilized.

3 Claims, 2 Drawing Sheets

OTHER PUBLICATIONS ite Material (PFC) and its Electrochemical Behavior".
Treatise for Technical Journal Tanso (Carbon) No. 152, pp. 106–114, 1992, Kawakubo et al., "Electrochemical Behavior of Carbon Microelectrodes Prepared by Using Graphite/Carbon Composite".
Treatise for Technical Journal of the Society of Analytical Chemistry, vol. 41, pp. 179–183 (1992), Kinoshita et al., "Preparation for Graphite Paste Electrode Containing Benzoquinone Fixed Nucleoside Oxidase and Its Behavior".
The Abstract of 41st Meeting of the Society of Analytical Chemistry held on Sep. 11–13, 1992, at Doshisha University in Kyoto, Kaneko et al., "A Trial for a Sensor Electrode Containing a Reactant in the Microholes of a Carbon Electrode".
Treatise for Technical Journal of the Society of Electrochemistry held in Dec., 1992, Kaneko et al., "Carbon Sensor Electrode Containing a Reactant in the Microholes".

① ~ ⑤  H$_2$O$_2$  1 ~ 5 mM (A) Fe(II)EDTA  1 mM

that the sensor can be utilized many times.

CARBON MICRO-SENSOR ELECTRODE AND METHOD FOR PREPARING IT

This is a division of U.S. application Ser. No. 07/905,767, filed Jun. 29, 1992, now U.S. Pat. No. 5,281,319.

BACKGROUND OF THE INVENTION (i) Field of the Invention

The present invention relates to a carbon microsensor electrode usable as, for example, an electrochemical detector, an environmental analysis sensor, a pathologic inspection sensor, and a probe electrode which is for the detection of an organism, a food and the like, and which is severely required to be harmless and non-toxic.

(ii) Description of the Prior Art

A rapid analysis using a sensor as a detecting tools which has been promptly developed in recent years in the wide field of an electrochemical determination has a very high selectivity and permits a high-sensitive measurement, and for this reason, this kind of rapid analysis begins to be often used in the analysis and evaluation of clinical samples and environmental samples each containing a trace amount of a component to be analyzed and many other kinds of compounds.

Recently, it has got very important to obtain biological information in vivo and in situ in a local site of an organism, for example, in a cell by the use of a sensor electrode capable of detecting such a specific material with a high sensitivity.

For this purpose, it is required that the electrode is set in the close vicinity of a target cell of the organism or thrust into the cell to give a physical, chemical or electrical irritation to the cell, so that a response material is released or a specific material is chemically produced, and the resultant material is detected and determined on the electrode.

Heretofore, as examples of such an electrode for determination, there have been developed a pH meter for measuring hydrogen ions, an ion sensor for detecting inorganic ions such as sodium ions, a sensor prepared by chemically modifying the surface of a carbon fiber (CF) or glass-like carbon (GC) with a complex or an organic material, various enzyme sensors such as a glucose sensor prepared by mixing a paste of a carbon paste (CP) electrode with an enzyme such as glucose oxidase and then coating the mixture with an ion permeable membrane, a biosensor having an immune metabolite and the like.

However, the chemically modified sensor, the enzyme sensor and the biosensor cannot withstand a long-term use except the pH meter and the inorganic ion sensor. That is, they have the drawback that their life is short.

In particular, most of the sensors in which the only surface of each electrode is chemically modified can scarcely withstand practical use.

SUMMARY OF THE INVENTION

An object of the present invention is to provide a sensor substrate which is usable for a long period of time, and a method for preparing the sensor substrate. This sensor substrate is applicable as a chemical modification sensor, a carbon sensor, a biosensor or the like and has a prolonged life. In necessary, a used portion of the sensor may be cut off to expose a new electrode surface, and this new electrode surface may be suitably treated with a material which does not impede an electrode reaction and which prevents a reactant from flowing out, whereby the sensor can be utilized many times.

That is, aspects of the present invention are as follows:

(1) A carbon micro-sensor electrode comprising a pure composite carbon, wire having many micropores extending to its surface and interior; and a reactant retained in said micropores which comprises at least one reactant selected from the group consisting of an enzyme, a metal complex compound, an organic compound and a metabolite.

(2) The carbon micro-sensor electrode according to the previous paragraph (1), further comprising an insulating coating layer, for preventing the reactant from flowing out, on the surface of the carbon wire.

(3) The carbon micro-sensor electrode according to the previous paragraph (2), further comprising the insulating coating material for preventing the reactant from flowing out being at least one selected from the group consisting of a silicon resin, a polyimide resin, a methacrylic resin, and another initial polymers thereof.

(4) A method for preparing a carbon micro-sensor electrode which comprises the steps of extruding, into a wire form having a desired diameter, a composition prepared by highly dispersing and mixing a crystalline carbon fine powder with an organic binder; calcining the wire up to a high temperature in an inert atmosphere or a non-oxidizing atmosphere to carbonize the contained organic binder and to thereby form the pure composite carbon wire having many micropores extending to its surface and interior; and then subjecting the carbon wire having many micropores to impregnation, adsorption, chemical modification or a combination thereof with a reactant which comprises at least one reactant selected from the group consisting of an enzyme, a metal complex compound, an organic compound and a metabolite.

(5) The method for preparing a carbon micro-sensor electrode according to the previous paragraph (4), further comprising the crystalline carbon fine powder being at least one selected from the group consisting of graphite whisker, highly oriented pyrolyric graphite, Kish graphite, natural graphite and artificial graphite.

(6) The method for preparing a carbon micro-sensor electrode according to the previous paragraph (4), further comprising the organic binder being an organic compound which effectively leaves a carbon residue when calcined in the inert atmosphere or the non-oxidizing atmosphere, and said organic compound being at least one selected from the group consisting of an organic polymer, its monomer or oligomer; a tar, a pitch, a carbonized pitch; a thermoplastic resin, and an initial polymer of a thermosetting resin.

(7) The method for preparing a carbon micro-sensor electrode according to the previous paragraph (4), further comprising the calcination and carbonization being achieved by performing a heat treatment at a temperature of 500° to 1500° C., and if necessary, carrying out a further heat treatment up to a temperature of 1500° to 3000° C. to form graphite.

DETAILED DESCRIPTION OF THE PREFERRED EMBODIMENTS

Figure 1:
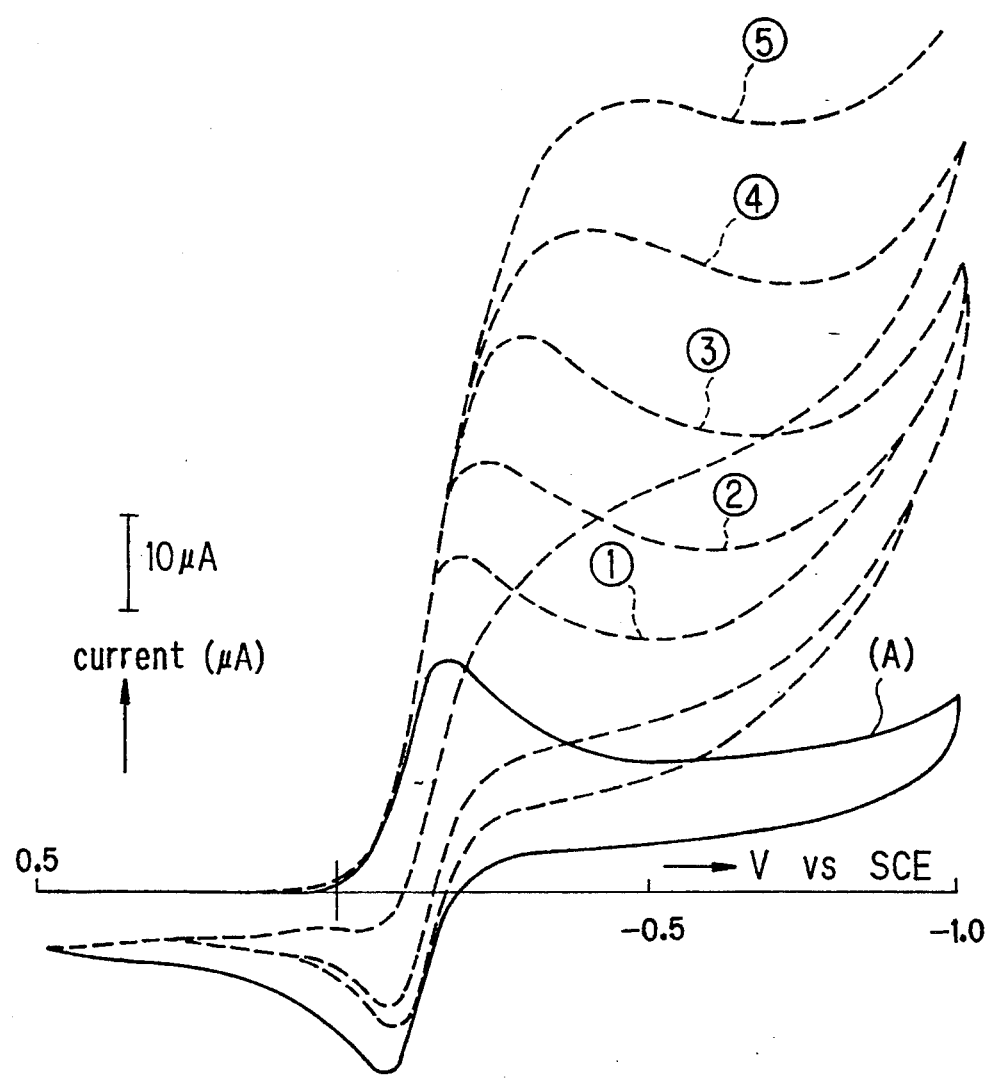
FIG. 1 shows a current potential curve (A) obtained in an acetic acid buffer solution (pH 5) containing 1 mM iron (III) EDTA compound on a carbon micro-sensor electrode of the present invention, and catalytic current potential curves (1) to (5) in the case that 1 to 5 mM of hydrogen peroxide are additionally present.

The present inventors have intensively researched to solve the above-mentioned problems. As a result, it has been found that the above-mentioned problems can be solved by preparing a sensor having a desired reactant therein or thereon. This kind of sensor can be prepared as follows: A long-term usable sensor substrate is first obtained by using a composite carbon material (a mechanical pencil lead material which is a composite material of natural graphite and an organic binder) having good characteristics as an electrode, and positively utilizing micropores formed in the preparing process, controlling of pore diameter in a preparation step, heightening its conductivity. The thus obtained sensor substrate, i.e., the porous composite carbon wire having many micropores extending to its surface and interior is then impregnated, adsorbed or chemically modified with a reactant such as an enzyme, a metal complex compound, an organic compound or a metabolite.

The carbon micro-sensor electrode which permits detecting a specific substance is required to meet the following requirements.

(1) Preparing the carbon micro-sensor electrode of a cellular scale which can give all of current, voltage and mechanical irritation to an organism.

(2) Not poisoning a measuring system, being safe even if the electrode remains in organism, and being usable in the inspection of foods.

(3) Having such mechanical strength as to permit the electrochemical inspection of an extremely small part of an organism or a food by thrusting the electrode into the small part.

(4) Having uniform sensor characteristics, and providing the better reproductivity of data and being capable of reliable determination.

(5) Being capable of stably measuring an electrode reaction by rapid coating, polishing or the like without requiring a special pretreatment and after-treatment.

(6) Being inexpensive and disposable.

From a wider viewpoint, the necessary requirements which the sensor electrode should have are as follows:

(1) Having a large potential window and a small blank current.

(2) Being capable of repeatedly, and in excellent reproductivity.

(3) Providing an active electrode reaction.

(4) Having uniform electrode properties.

(5) Containing less impurities, and not interfering with the electrode reaction.

(6) Easy handling and the pretreatment.

In the present invention, a pure carbon wire having many micropores extending to its surface and interior is subjected to impregnation, adsorption, chemical modification or a combination thereof with a reactant such as an enzyme, a metal complex compound, an organic compound or a metabolite to obtain a carbon micro-sensor having the desired reactant therein or thereon.

Next, reference will be made to a preparation method of the carbon micro-thin wire having many micropores. The porous carbon micro-thin wire of the present invention can be obtained by extruding, into a straight form having a desired diameter, a composition formed by highly dispersing and mixing a crystalline carbon fine powder with an organic binder; and then calcining the molded composition up to a high temperature in an inert atmosphere or a non-oxidizing atmosphere to achieve carbonization. At this time, a part of the organic binder decomposes, gasifies and gets away, so that the micropores extending to its surface and interior are formed therein.

The crystalline carbon fine powder which is mixed with the organic binder will be described in the following.

In order to permit the good electrode reaction, it is necessary to form the composite carbon material in which its orientation is oriented so that crystal edge (edge surfaces) of highly developed graphite crystals may be arranged vertically to the surface of the electrode. Therefore, preferable examples of the crystalline carbon fine powder include graphite whisker, highly oriented pyrolyric graphite (HOPG), Kish graphite, crystalline natural graphite and artificial graphite. The particle diameter of the crystalline carbon fine powder is preferably under most several $\mu$m, depending upon the diameter of the desired electrode.

The blend contents of the crystalline carbon fine powder is in the range of 30% to 90%, preferably 50% to 70% of the uncarbonized linear compound, depending upon the kind of organic binder to be used and the diameter of the desired electrode.

On the other hand, the organic binder is an organic compound which can effectively leave a carbon residue when calcined in an inert atmosphere or a non-oxidizing atmosphere, and a typical example of the organic binder is one or a mixture of two or more selected from the group consisting of an organic polymer, its monomer and oligomer; a tar, a pitch, a carbonized pitch; a thermoplastic resin, and an initial polymer of a thermosetting resin.

The above-mentioned organic polymer in addition to the undermentioned thermoplastic resin and thermosetting resin are as follows. Examples of the organic polymer include lignin, cellulose, tragacanth gum, natural gum and derivatives thereof, natural polishers having a condensed polycyclic aromatic moiety in the basic structure of each molecule, such as saccharides, chitin and chitosan, and a synthetic high polymers such as a formalin condensation product of naphthalenesulfonic acid, indanthrene dyes derived from dinitronaphthalene, pyrene, pyranthrone, violanthrone, benzanthrone and the like, and intermediates thereof.

Examples of the thermoplastic resin include usual thermoplastic resins such as polyvinyl chloride, polyacrylonitrile, polyvinylidene chloride, chlorinated vinyl chloride, polyvinyl acetate, polyvinyl alcohol, polyvinyl pyrrolidone, ethyl cellulose, carboxylmethyl cellulose and polyvinyl chloride-vinyl acetate copolymer, and heat-resistant thermoplastic resins such as polyphenylene oxide, poly-para-xylene, polysulfone, polyimide, polyamide imide, polybenzimidazole and polyoxydiazole.

Examples of the thermosetting rein include a phenolic resin, a furan resin, an epoxy resin, a xylene resin and a COPNA resin. These examples can flow and form an intermolecular crosslinkage to become three-dimensional and to cure, when heated, and they can provide a high carbon yield, even if any special treatment to carbon precursor formation is not carried out.

Examples of the pitch include petroleum pitch, coal tar pitch, asphalt and a carbonized material (a material treated at a temperature of 400° C. or less) of the pitch, a synthetic resin or the like.

Next, reference will be made to the preparation method of the carbon micro-thin wire having many micropores. The crystalline composite organic thin wire (the green thin wire) which has not been subjected to the calcination yet can be obtained by selecting one or more of the organic binders from the group consisting of the above-mentioned natural polymer, synthetic polymer, thermosetting resin, thermoplastic resin, pitch and the like; blending the selected organic binder with the crystalline carbon fine powder suitably selected in compliance with a purpose; and then dispersing them sufficiently by a Henshel mixer or the like.

If necessary, there can be added a resin having a low carbon yield or a resin showing no carbon yield as a pore forming agent, a plasticizer, a solvent and the like. The blend is sufficiently mixed and dispersed by the use of a kneader such as a pressing kneader or two rolls which can highly provide shearing force, and it is then granulated by means of a pelletizer. Afterward, the pellets are extruded into a wire form having a desired diameter by the use of a screw type extruder to obtain a carbon micro-thin wire as an electrode substrate.

Next, this thin wire is treated for 10 hours in an air oven heated to 180° C. to form a precursor (carbon precursor) wire.

Furthermore, the wire is carbonized by slowly heating itself up to 1000° C. in a nitrogen gas under the control of a temperature rise rate, thereby obtaining a carbon micro-thin wire having many micropores.

In the case of a certain purpose, the thin wire may further be thermally treated up to 2500° C. in vacuum or in an argon gaseous phase to make the whole wire graphite.

Here, the crystalline carbon fine powder which is used as the raw material may be subjected to a particle size distribution adjustment so as to give rise to a steric hindrance and to thereby form the suitable micropores, and a resin having a low carbon yield or a resin showing no carbon yield may be blended as a pore forming agent. The more suitable carbon micro-thin wire having many micropores can be obtained for impregnating, adsorbing or chemically modifying with an enzyme, a metal complex compound, an organic compound, a metabolite or the like.

Next, reference will be made to a process in which the thus obtained wire having many micropores therein and thereon is impregnated, adsorbed or chemically modified with a reactant such as an enzyme, a metal complex compound, an organic compound, a metabolite or the like to retain the desired reactant in or on the thin wire.

In the first place, preparations are made for the impregnation of the porous carbon thin wire having the micropores therein and thereon with a reactant such as an enzyme, a metal complex compound, an organic compound or a metabolite. In order to introduce a reactant such as an enzyme, a metal complex compound, an organic compound or a metabolite into the micropores of the carbon substrate, the reactant is first preferably liquefied, if it is solid and if it is not denatured or changed when liquefied.

For the metallic complexes and some of the organic compounds, the above-mentioned liquefaction is necessary.

An unstable reactant for oxygen such as the enzyme or the metabolite is preserved in an aqueous solution or an organic solvent together with a stabilizing agent such as a vitamin. Of the organic compounds which are not water-soluble, a substance which is dispersible in silicone oil or the like is uniformly dispersed in the silicone oil having a low viscosity.

The reactant which is stable in a polar and volatile organic solvent is preferably dissolved or dispersed in this kind of organic solvent.

Reference will be made to the technique of impregnating the porous carbon thin wire having the micropores therein and thereon with a liquid reactant such as an enzyme, a metal complex compound, an organic compound or a metabolite which has already got ready. In order to fully impregnate the porous carbon thin wire with the reactant up to its center without denaturing the same, a technique is necessary which permits fully introducing the reactant into the micropores up to the center without breaking the substrate.

Therefore, the fundamental concept of this technique resides in that air in the micropores of the porous carbon substrate is expelled by some means and the reactant is then introduced thereinto. In order to expel air and to introduce the liquid containing the desired impregnation substance, the following methods can be employed.

(1) Heat impregnation method.
(2) Impregnation method under reduced pressure.
(3) Utilization of capillary action.

(1) The heat impregnation method is used in the case that the porous carbon material is impregnated with the thermally stable reactant dissolved in silicone oil or water. This method comprises immersing, in a solution containing the reactant, a part or all of the carbon substrate which is used to prepare a sensor, while heating the solution at a temperature of about 100° to 150° C., and then maintaining the same temperature until air bubbles have not appeared any more, whereby the substrate having the micropores is impregnated with the solution.

(2) The impregnation method under reduced pressure is suitable for the case that the reactant or its solution is not resistant to heat or is volatile.

This method comprises placing a solution containing the reactant in a vacuum desiccator, reducing the pressure in the desiccator by the sufficient suction of a water jet pump, and then impregnating the carbon substrate with the solution.

(3) The utilization of capillary action is suitable for the case that the reactant is dissolved in the organic solvent having a good wettability to carbon or the case that the reactant is so extremely volatile as not to be suitable for the impregnation under reduced pressure.

After the carbon substrate has been fully impregnated with the reactant in the above-mentioned manner, the thus obtained electrode is coated with a glass-like resin or a polyimide resin to insulate it.

This electrode can be used as a disk semi-microsensor for the detection of a specific substance again and again by breaking off the used tip portion of the electrode while the reactant keeps stability.

EXAMPLES

The present invention will be described in more detail in reference to examples, but the scope of the present invention should not be limited to these examples.

EXAMPLE 1

In a Henschel mixer were placed 40% by weight of a chlorinated vinyl chloride resin (Nippon Carbide Co., Ltd.; T-742), 25% by weight of Kish graphite (Kouwa Seikou Co., Ltd.; KH; average particle diameter 5 μm), 30% by weight of kish graphite (Kouwa Seikou Co., Ltd.; HC-A15; average particle diameter 15 μm), 5% by weight a fatty acid ester (Nippon Oil & Fats Co., Ltd.; Unister H) as a resin which did not show any carbon yield and 20% by weight of a diallyl phthalate monomer plasticizer, as materials of a porous carbon thin wire. They were then mixed by the mixer and then sufficiently repeatedly kneaded by the use of two rolls for mixing whose surface temperature was maintained at 120° C. to obtain a sheetlike composition. Afterward, this composition was pelletized by a pelletizer to obtain a composition for molding. These pellets were extruded at 130° C. by a screw extruder having a 0.7 mm diameter die, while deaerated, and the extruded article was fixed on a frame and then treated for 10 hours in an air oven heated at 180° C. to form a carbon precursor wire. Next, the wire was calcined by heating itself at a temperature rise rate of 10° C./hour at 500° C. or less and at a temperature rise rate of 50° C./hour at 500°–1000° C., maintaining it at 1000° C. for 3 hours, and then naturally cooling it. For a certain purpose, the wire might be heated up to 2500° C. in vacuum or in an argon gaseous phase to make the whole wire graphite.

As a result, a porous carbon thin wire having a diameter of 0.5 mm was obtained. This carbon thin wire was then cut into a length of 50 mm to obtain substrates for porous carbon micro-electrodes.

Each electrode substrate having the micropores was impregnated under reduced pressure and packed with an iron ethylenediaminetetraacetic acid (iron EDTA) compound which was similar to a peroxidase, thereby preparing a sensor electrode.

The iron (II) EDTA compound was rapidly reacted with oxygen or hydrogen peroxide to change into iron (III) EDTA. This reaction catalytically proceeds as shown by the following formulae, and therefore it is possible to detect or determine a trace amount of hydrogen peroxide and the like.

$$Fe\ (III)\ EDTA + e \rightarrow Fe\ (II)\ EDTA \quad (1)$$

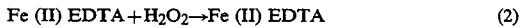

$$Fe\ (II)\ EDTA + H_2O_2 \rightarrow Fe\ (II)\ EDTA \quad (2)$$

In most of the oxidizing reactions in a biological system, hydrogen peroxide is produced, and therefore it is important to detect a trace amount of hydrogen peroxide. An electric potential was maintained so that the charge of iron in the iron EDTA compound introduced into the sensor electrode might be kept divalent, and there was detected an electrochemical catalytic reaction which could be represented by a reduction wave of iron (III) EDTA due to hydrogen peroxide produced in the solution. FIG. 1 shows the increase of current values depending upon the concentration of hydrogen peroxide and the change of the waveform of a catalytic current. Prior to the use of the sensor electrode, the electrode was immersed in a dilute benzene solution of polymethyl methacrylate (PMMA) which would be a coating film not interfering with the electrode reaction, whereby the electrode was spin-coated. As a result, the iron (II) EDTA compound could be prevented from flowing out of the electrode into the solution.

Figure 2:
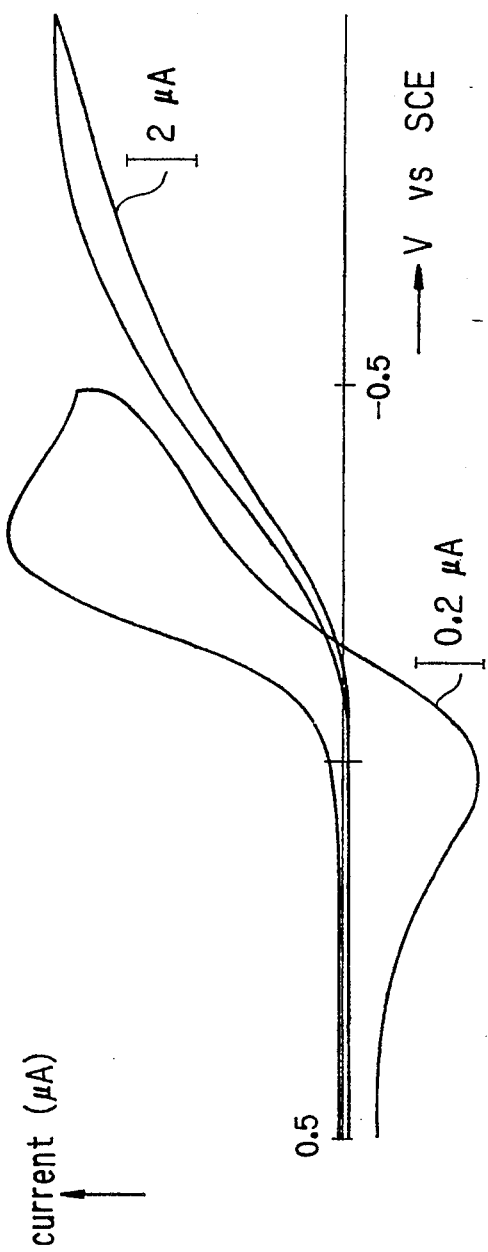
FIG. 2 shows a current potential curve denoted in an acetic acid buffer solution (B) and a current potential curve obtained in 5 mM of hydrogen peroxide-an acetic acid buffer solution (pH 5) on a carbon micro-sensor electrode (diameter 0.5 mm and length 2 mm) of the present invention.

FIG. 2 shows a current potential curve represented by this sensor electrode in a solution containing 1 mM of hydrogen peroxide. Since the sensor electrode of the present invention was substantially uniformly impregnated with the iron (II) EDTA compound up to its center, it could be used again and again even after once used, by cutting off the used portion of the electrode and then coating the new electrode surface with PMMA.

According to the present invention, there can be provided a reactant-containing type carbon micro-sensor electrode which has a long life and a good insulating film, can be used for a long period of time in contrast to conventional sensors and sensor electrodes, and permits detecting a specific substance in many biological samples and foods in situ.

That is, the present invention is directed to a sensor electrode having a long-time usable structure by introducing a reactant such as an enzyme into the micropores formed under control in the electrode itself, and when a spin coating process is used to insulate the surface of the electrode, the practical thin state of the micro-sensor electrode can be maintained.

Furthermore, the carbon electrode of the present invention can be very economically used again and again by cutting off the used portion of the electrode, and then coating the new electrode surface with polymethyl methacrylate or the like which does not impede the electrode reaction, so as to prevent the reactant from flowing out of the electrode.

What is claimed is:

1. A carbon micro-sensor electrode comprising a composite carbon single wire having many micropores extending to its surface and interior; and a reactant retained in said micropores, which comprises at least one reactant selected from the group consisting of an enzyme, a metal complex compound, an organic compound and a metabolite.

2. The carbon micro-sensor electrode according to claim 1, further comprising an insulating coating layer, for preventing the reactant from flowing out, on the surface of the carbon wire.

3. The carbon micro-sensor electrode according to claim 2, further comprising the insulating material is at least one selected from the group consisting of a silicon resin, a polyimide resin, a methacrylic resin, and a monomer, an oligomer and an initial polymer thereof.

* * * * *